United States Patent [19]

Wallach

[11] Patent Number: 4,531,963

[45] Date of Patent: Jul. 30, 1985

[54] USE OF PHENYL HYDRAZINES FOR SEED BIOSTIMULATION OR THE TREATMENT OF LIPOXYGENASE MEDIATED SEED DETERIORATIONS

[75] Inventor: Donald P. Wallach, Kalamazoo, Mich.

[73] Assignee: The Upjohn Company, Kalamazoo, Mich.

[21] Appl. No.: 431,906

[22] Filed: Sep. 30, 1982

[51] Int. Cl.$^3$ .................. A01N 33/06; A01N 33/08
[52] U.S. Cl. ...................................... 71/77; 71/90; 71/121; 514/826; 514/863
[58] Field of Search .................. 71/77, 121, 90

[56] References Cited

PUBLICATIONS

Jacques-Felix et al., Chem. Abst. vol. 61, 6294g.

Primary Examiner—Catherine L. Mills
Attorney, Agent, or Firm—Lawrence T. Welch

[57] ABSTRACT

The present invention provides a method of treating certain deleterious conditions mediated by the action of lipoxygenases in mammals and seeds using certain phenyl hydrazines. Also provided is a method for seed biostimulation using these phenyl hydrazines.

4 Claims, No Drawings

USE OF PHENYL HYDRAZINES FOR SEED BIOSTIMULATION OR THE TREATMENT OF LIPOXYGENASE MEDIATED SEED DETERIORATIONS

BACKGROUND

The present invention relates to a new use of known compositions. More particularly, the present invention relates to the prevention of adverse conditions mediated by the action of lipoxygenase in plant and animal systems using certain hydrazines. The present invention further provides a method of seed biostimulation using certain hydrazines.

In mammalian metabolism, arachidonic acid is transformed to 12-L-hydroperoxy-5,8,10,14-eicosatetraenoic acid by the action of lipoxygenase. See, Hamberg, et al, Proc. Nat. Acad. Sci. 71:3400–3404 (1974). 12-L-Hydroperoxy-5,8,10,14-eicosatetraenoic acid has been shown to be a mediator of psoriasis in Hammarstrom, et al, Proc. Nat. Acad. Sci. 72:5230–5134 (1974), and chemotactic and inflammatory responses (see, Goetzl, et al, Journal of Immunology 120:526 (1978)).

Thus, an agent which inhibits the action of lipoxygenase would also be useful in treating or preventing untoward conditions associated with 12-L-hydroperoxy-5,8,10,14-eicosatetraenoic acid.

In plants, lipoxygenases catalyze the conversion of polyunsaturated fatty acids to hydroperoxy acids and epoxides. These compounds are reactive and form complex addition products with the protein components of leguminous oilseeds. This process is a major contributor to the off-flavors and orders of oil seeds stored for protracted periods of time. Further, lipoxygenases, by their oxidative proclivities for the lipid components of such seeds, contribute to the deterioration of germenation percentage, and general viability.

Therefore, compounds which inhibit the action of lipoxygenase would be useful in the treatment of inflammatory conditions where it is desirable to prevent migration of polymorphonuclear leukocytes to the inflammatory site, the prevention of chemotactic responses of leukocytes and would further be useful for the retardation of spoilage in oil seeds and pulse seeds as a result of lipoxygenase activity. By pulse seeds is meant the edible seeds of leguminous plants, i.e., peas, peanuts, and the like.

A common problem associated with many seeds (e.g., soybeans) is their relatively low viability, making them unsuitable for use beyond the first season. Further, the rate of germination of certain seeds even when fresh is relatively low. Therefore, what is needed in the art is a method to increase the rate of seed germination.

The present invention provides a class of certain phenyl hydrazines which are useful as inhibitors of lipoxygenase derived from both plant and animal source and are thus useful for the purposes described above.

PRIOR ART (1-Benzyl-1-phenyl)hydrazine is disclosed in Hayes, B. T. and T. S. Stevens; Reduction of Nitrosamines to Hydrazines; J. Chem. Soc. pp 1088–1089 (1970). (1-Naphthyl)hydrazine is disclosed in El-Sebae, A. H., S. A. Soliman and N. Bakry; Alexandria J. Agr. Res. 21:119–124 (1973). (2-Chlorophenyl)hydrazine is disclosed in El-Sabae, supra, and Marousek, V., et al., Sb. Vys. Sk. Chem.—Technol. Praye, Org. Chem. Technol. C18:67–74 (1973). [2-(Trifluoromethyl)phenyl]hydrazine is disclosd in Forbes, E. J., et al.; Tetrahedron, 8 67–72 (1960). [1-Phenyl-1-(tetrahydro-3-thienyl)]hydrazine is disclosed in Argyle, C. S., et al., J. Chem. Soc. (21) pp 2156–2170 (1967). [3-(Trifluoromethyl)phenyl]hydrazine is disclosed in Forbes, E. J., et al., Tetrahedron, 8, 67–72 (1960). [2-Chloro-5-(trifluoromethyl)-phenyl]hydrazine is disclosed in Ger. Offen. 2,446,218. The lipoxygenase inhibitory activity of certain hydrazones is described in Wallach, et al., Biochim. Biophys. Acta. 663:361 (1981) and the therapeutic use of these compounds is described in copending application 350,553, filed 19 Feb. 1982. Copending application 402,082, filed 26 July 1982, discloses certain lipoxygenase inhibitors as seed biostimulants.

SUMMARY OF THE INVENTION

The present invention particularly provides:

(1) A method for treating or preventing lipoxygenase-mediated conditions (LMC) in a mammal suffering from or susceptible to said LMC which comprises:

administering to said mammal a compound of the Formula I, or a pharmaceutically acceptable salt or hydrate thereof,

$$N(R_1)(R_2)NH_2 \qquad I,$$

wherein $R_1$ is
(a) phenyl,
(b) $(C_7-C_{12})$aralkyl,
(c) biphenyl,
(d) naphthyl,
(e) tetrahydrothienyl, or
(f) any of the previous groups substituted by 1–5 substituents selected from the following:
  (i) halogen,
  (ii) $(C_1-C_3)$alkyl, or
  (iii) trifluoromethyl, with the proviso that no more than 2 substituents are alkyl and no more than 1 asubstituent is trifluoromethyl;

wherein $R_2$ is
(a) hydrogen,
(b) $(C_7-C_{12})$aralkyl,
(c) tetrahydrothienyl, or
(d) $(C_7-C_{12})$aralkyl substituted by 1–5 substituents selected from the following:
  (i) halogen,
  (ii) $(C_1-C_3)$alkyl, or
  (iii) trifluoromethyl, with the proviso that no more than 2 substituents are alkyl and no more than 1 substituent is trifluoromethyl; with the further proviso that $R_2$ can be other than hydrogen only when $R_1$ is phenyl or substituted phenyl, in an amount effective to treat or prevent said LMC;

(2) A method for treating or preventing lipoxygenase mediated seed deteriorations (LMSD) in oil or other seeds susceptible to said LMSD which comprises:

contacting said seeds with a compound of the Formula I,

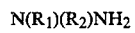

$$N(R_1)(R_2)NH_2 \qquad I,$$

or an acid addition salt or hydrate thereof,
wherein $R_1$ is
(a) phenyl,
(b) $(C_7-C_{12})$aralkyl,
(c) biphenyl,
(d) naphthyl,
(e) tetrahydrothienyl, or (f) any of the previous groups substituted by 1–5 substituents selected from the following:
  (i) halogen,
  (ii) (C$_1$–C$_3$)alkyl, or
  (iii) trifluoromethyl, with the proviso that no more than 2 substituents are alkyl and no more than 1 asubstituent is trifluoromethyl;
wherein R$_2$ is
(a) hydrogen,
(b) (C$_7$–C$_{12}$)aralkyl,
(c) tetrahydrothienyl, or
(d) (C$_7$–C$_{12}$)aralkyl substituted by 1–5 substituents selected from the following:
  (i) halogen,
  (ii) (C$_1$–C$_3$)alkyl, or
  (iii) trifluoromethyl, with the proviso that no more than 2 substituents are alkyl and no more than 1 substituent is trifluoromethyl; with the further proviso that R$_2$ can be other than hydrogen only when R$_1$ is phenyl or substituted phenyl, in an amount effective to treat or prevent said LMSD; and (3) a method for promoting the germination of oil seeds comprising contracting a compound of the formula I $$N(R_1)(R_2)NH_2 \qquad I,$$

or an acid addition salt or hydrate thereof,
wherein R$_1$ is
(a) phenyl,
(b) (C$_7$–C$_{12}$)aralkyl,
(c) biphenylyl
(d) napthyl,
(e) tetrahydrothienyl, or
(f) any of the previous groups substituted by 1–5 substituents selected from the following:
  (i) halogen,
  (ii) (C$_1$–C$_3$)alkyl, or
  (iii) trifluoromethyl, with the proviso that no more than 2 substituents are alkyl and no more than 1 substituent is trifluoromethyl;
wherein R$_2$ is
(a) hydrogen,
(b) (C$_7$–C$_{12}$)aralkyl,
(c) tetrahydrothienyl, or
(d) (C$_7$–C$_{12}$)aralkyl substituted by 1–5 substituents selected from the following:
  (i) halogen,
  (ii) (C$_1$–C$_3$)alkyl, or
  (iii) trifluoromethyl, with the proviso that no more than 2 substituents are alkyl and no more than 1 substituent is trifluoromethyl; with the further proviso that R$_2$ can be other than hydrogen only when R$_1$ is phenyl or substituted phenyl.

The carbon atom content of various hydrocarbon-containing moieties is indicated by a prefix designating the minimum and maximum number of carbon atoms in the moiety, i.e., the prefix (C$_i$–C$_j$) indicates a moiety of the integer "i" to the integer "j" carbon atoms, inclusive. Thus (C$_1$–C$_3$)alkyl refers to alkyl of one to 3 carbon atoms, inclusive, or methyl, ethyl, propyl, and isopropyl.

Examples of alkyl of one to 3 carbon atoms, inclusive, are methyl, ethyl, propyl, and isomeric forms thereof.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

The hydrazines of the present invention are well known, readily available compounds and are prepared by the methods described in Laing, "Rodd's Chemistry of Carbon Compounds," Vol. III, Chap. 12, pp. 214–247 (1973) and Timberlake, et al., "The Chemistry of Hydrazo, Azo, and Azoxy Groups," The Chemistry of Functional Groups, Chap. 4, pp. 69–83 (1975). See, also, the references described under "Prior Art."

By lipoxygenase mediated condition (LMC) in mammals is meant all untoward conditions which are mediated by the action of lipoxygenase. These conditions include e.g., psoriasis and asthma as set forth above.

The precise mechanisms of the disease processes or conditions which stimulate this portion of the arachidonic acid cascade are not clearly understood. The method of this invention works by preventing the action of lipoxygenase despite the stimulating conditions. Thus, the method of this invention is suitable for treating seemingly unrelated diseases whose common element is the mediation of lipoxygenase. The term "lipoxygenase mediated conditions" (LMC) includes all untoward conditions or symtoms which are the result of the excessive stimulation of this portion of the arachidonic acid cascade. Some disease processes and conditions which stimulate the action of lipoxygenase include: genetic abnormalities, exposure to allergenic substances, and inflammatory diseases. The method of this invention is also useful in treating an LMC caused by any other disease process or condition.

The method of this invention could be used on any mammal whose metabolic system includes the portion of the arachidonic acid cascade mediated by the actions of lipoxygenases. The mammals which are preferred are generally domesticated animals and humans. Humans are the most preferred mammals to be treated by the method of this invention.

The method of this invention is useful both in treating an LMC or symptom which has already manifested itself in the mammal as well as the prevention of these conditions or symptoms in mammals particularly susceptible to them. Employment of the method of this invention prior to the development of an LMC would prevent the formation of the 12-L-hydroperoxy-5,8,10,14-eicosatetraenoic acids and similar products necessary for such conditions. Thus, the compounds of this invention could be administered to persons suffering from asthma or similar conditions prior to exposure to stimulating conditions. In a like manner, a physician or veterinarian could readily determine other mammals or persons susceptible to an LMC.

Once an LMC has manifested itself a physician or veterinarian could readily determine the necessity of employing the process of this invention.

The actual inhibition of lipoxygenase by the method of this invention takes place on a cellular level. Administration of the compound of this invention can thus be by any manner which will allow for lipoxygenase inhibition in the affected tissues or organs. The preferred route in most cases would be to systemically administer the compounds, i.e., to allow them to enter the mammal's bloodstream and thus be administered throughout the mammal's system.

Since the diseases or conditions formed as a result of this portion of the arachidonic acid cascade are varied, methods of administering these compounds must depend on the particular LMC sought to be treated. Regardless of the route of administration selected the compounds used in the process of the present invention are formulated into pharmaceutically acceptable dosage form by conventional methods known to the pharmaceutical art. Since these phenyl hydrazones are somewhat insoluble they may need to be formulated into micronized suspensions.

Thus, the compounds are administered orally in forms such as pills, capsules, solutions or suspensions. They may also be administered rectally or vaginally in forms such as suppositories or bougies. They may also be introduced intravenously, subcutaneously, or intramuscularly using sterile injectable forms known to the pharmaceutical art.

In general the preferred form of administration is orally.

The dosage regimen for preventing or treating lipoxygenase mediated conditions (LMC) by the compounds of this invention is selected in accordance with a variety of factors, including the type, age, weight, sex and medical condition of the mammal, the severity of the LMC and the particular compound employed. An ordinarily skilled physician or veterinarian will readily determine and prescribe the effective amount of the anti-LMC agent to prevent or arrest the progress of the condition. In so proceeding the physician or veterinarian could employ relatively low dosages at first, subsequently increasing the dose until a maximal response is obtained.

Initial dosages of the compounds of this invention can be from 10 to 50 mg per kg per 8 hrs. orally. When other forms of administration are employed, equivalent doses are administered. When dosages beyond 20 mg per kg per 8 hrs. are employed, care should be taken with each subsequent dose to monitor possible toxic effects.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate, and the like. These salts may also be in hydrated form.

The compounds of this invention are also employed to prevent lipoxygenase-mediated seed deteriorations (LMSD) in oil seed crops, e.g., peanuts, soybeans, cottonseed, sunflower seeds, jojoba seeds, and certain edible seeds where the actions of lipoxygenases on endogenous lipids results in the destruction of natural flavors and the development of off flavors due to hydroperoxy acids, and lipid oxidation in oil seeds because of their reactions with cellular proteins.

The compounds of the present invention are also useful to promote seed germination in these same classes of seeds.

For both these latter purposes, the phenyl hydrazines must be contacted with the seeds. Thus, these phenyl hydrazines are sprayed on seeds, or the seeds are washed in a bath in which a phenyl hydrazine is dissolved or suspended at a concentration of from about $10^{-3}$ to about $10^{-6}$M, preferably from about $1\times10^{-4}$M to about $1\times10^{-5}$M. Complete inhibition of lipoxygenase activity results at these concentrations, thus preventing LMSD. Similarly, seed biostimulation is accomplished at this concentration, as seen by Example 2 below.

DESCRIPTION OF THE PREFERRED EMBODIMENTS

The efficacy of the compounds employed in the present invention as inhibitors of lipoxygenase is shown by the following Example.

EXAMPLE 1

The soybean lipoxygenase assay was carried out as follows: To four oxygraph cells is added 2.5 ml of 0.033M Ammediol HCl buffer, pH 8.5, 0.03 ml of soybean lipoxygenase (0.15 mg). This mixture is incubated for 3 minutes before adding 0.05 ml of 0.01M arachidonic acid. Oxygen uptake is measured with the Yellow Springs oxygraph as described above. Conditions are the same except that the MV span on the recorder is set at 10. Calculations are made as above.

Pulse seeds were obtained from The Country Life, Oak Have, Pullman, MI. Twenty-five grams of seeds were weighed out and put in a chilled Waring blender head with four volumes of cold 0.2° C.) 0.154M KCl. Seeds were blended for 60-90 sec at maximal speed. The homogenate was centrifuged for 10 min and the supernatant fluid decanted and filtered through glass wool. This supernatant is the crude pulse seed enzyme used in the assay.

Pulse seed enzyme assays are as follows. To 2.4 ml of 0.1M potassium phosphate buffer, pH 6.0, in each of 4 oxygraph cells is added 0.1 ml of enzyme. The electrodes are inserted in the cells and the mixture is incubated with stirring for 3 min at 37° C. to allow for temperature equilibration.) 0.05 ml of 0.01M arachidonic acid is added to each cell and oxygen uptake is recorded under the following conditions: 37° C., 5 MV total span, air setting, 1:1 scale expansion and medium chart speed. The slopes of initial oxygen consumption are then calculated as the measure of the rate of $O_2$ uptake. Samples are run in duplicate and the mean and standard deviation of the slopes are then calculated.

Table 1 summarizes effects of active hydrazines on soybean lipoxygenase in order of decreasing potency.

Table 2 summarizes results obtained when active hydrazines were tested against 3 pulse seed lipoxygenases.

TABLE 1

Inhibitory Effects of Hydrazines on Soybean Lipoxygenase

| Compound | $I_{50}$ (M) |
|---|---|
| ($\alpha,\alpha,\alpha$-trifluoro-m-tolyl)-hydrazine, hydrochloride | $2.06 \times 10^{-7}$ |
| (o-chlorophenyl)-hydrazine, hydrochloride | $2.4 \times 10^{-7}$ |
| 1-benzyl-1-phenyl-hydrazine, hydrochloride | $2.47 \times 10^{-7}$ |
| ($\alpha,\alpha,\alpha$-trifluoro-o-tolyl)-hydrazine, hydrochloride | $3.72 \times 10^{-7}$ |
| 1-phenyl-1-(tetrahydro-3-thienyl)-hydrazine, hydrochloride | $1.36 \times 10^{-6}$ |
| (6-chloro-$\alpha,\alpha,\alpha$-trifluoro-m-tolyl)-hydrazine | $2.13 \times 10^{-6}$ |
| (1-naphthyl)-hydrazine, hydrochloride | $2.2 \times 10^{-6}$ |

TABLE 2

Results ($I_{50}$) with Hydrazines on Some Pulse Seed Lipoxygenases

| Compound | Black Bean (M) | Yellow Pea (M) | Lentil (M) |
|---|---|---|---|
| ($\alpha,\alpha,\alpha$-trifluoro-m-tolyl)-hydrazine, | $2.4 \times 10^{-6}$ | $1 \times 10^{-5}$ | $2.84 \times 10^{-6}$ |

TABLE 2-continued

Results ($I_{50}$) with Hydrazines on Some Pulse Seed Lipoxygenases

| Compound | Black Bean (M) | Yellow Pea (M) | Lentil (M) |
|---|---|---|---|
| hydrochloride (o-chlorophenyl)-hydrazine, hydrochloride | $2.21 \times 10^{-6}$ | $2 \times 10^{-5}$ | $3.28 \times 10^{-6}$ |
| 1-benzyl-1-phenyl-hydrazine, hydrochloride | $2.4 \times 10^{-7}$ | $6.33 \times 10^{-7}$ | $4.75 \times 10^{-7}$ |
| ($\alpha,\alpha,\alpha$-trifluoro-o-tolyl)-hydrazine, hydrochloride | $2.57 \times 10^{-6}$ | $6.6 \times 10^{-6}$ | $3.58 \times 10^{-6}$ |
| 1-phenyl-1-(tetrahydro-3-thienyl)-hydrazine, hydrochloride | $9.05 \times 10^{-6}$ | $9.05 \times 10^{-6}$ | $7.6 \times 10^{-6}$ |
| (6-chloro-$\alpha,\alpha,\alpha$-trifluoro-m-tolyl)-hydrazine | $4.42 \times 10^{-6}$ | $2.4 \times 10^{-5}$ | $1 \times 10^{-5}$ |
| (1-naphthyl)-hydrazine, hydrochloride | $1.16 \times 10^{-5}$ | $9.5 \times 10^{-5}$ | $9.5 \times 10^{-5}$ |

EXAMPLE 2

$\alpha,\alpha,\alpha$-Trifluoro-o-tolyl-hydrazine was dissolved in ethanol and applied to soybean seed in a small seed treater at 4 ml per 250 g seed. This rate thoroughly wetted the seed surface.

The seeds were subjected to an accelerated aging treatment. The accelerated aging treatment exposed the seed to nearly 100% relative humidity at 41° C. for 48 hr (suggested procedures by Assoc. Official Seed Analysts, Vigor Testing Subcommittee). The results are set forth in Table 2.

SEED TREATMENT

| Material | Concentration (Molar) | Standard Germination (1) (%) | Germination After Aging (1) (%) | Seedling Fresh Wt. (2) (mg) |
|---|---|---|---|---|
| Control (untreated) | | 91 | 92 | 519 |
| Hydrazine | $1 \times 10^{-4}$ | 92 | 92 | 646* |
| | $5 \times 10^{-5}$ | 92 | 90 | 604* |
| | $1 \times 10^{-5}$ | 91 | 91 | 575 |

(1) Average germination for 3 seedlots
(2) Vigor test conducted on only one seedlot
*Indicates statistically significant improvement over control at a 99% level of confidence.

CHART A

Arachidonic Acid

→ Lipoxygenase →

12-L-Hydroperoxy-5,8,10,14-Eicosatetraenoic Acid

I claim:
1. A method for treating or preventing lipoxygenase mediated seed deteriorations (LMSD) in oil or other seeds susceptible to said LMSD which comprises: contacting said seeds with a compound selected from the group consisting of
    ($\alpha,\alpha,\alpha$-trifluoro-m-tolyl)-hydrazine;
    (o-chlorophenyl)-hydrazine;
    1-benzyl-1-phenyl-hydrazine;
    ($\alpha,\alpha,\alpha$-trifluoro-o-tolyl)-hydrazine;
    1-phenyl-1-(tetrahydro-3-thienyl)-hydrazine;
    (6-chloro-$\alpha,\alpha,\alpha$-trifluoro-m-tolyl)-hydrazine; and
    (1-naphthyl)-hydrazine;
or an acid addition salt or hydrate thereof; in an amount effective to treat or prevent said LMSD.

2. A method for promoting the germination of oil seeds comprising contacting said seeds with a compound selected from the group consisting of:
    ($\alpha,\alpha,\alpha$-trifluoro-m-tolyl)-hydrazine;
    (o-chlorophenyl)-hydrazine;
    1-benzyl-1-phenyl-hydrazine;
    ($\alpha,\alpha,\alpha$-trifluoro-o-tolyl)-hydrazine;
    1-phenyl-1-(tetrahydro-3-thienyl)-hydrazine;
    (6-chloro-$\alpha,\alpha,\alpha$-trifluoro-m-tolyl)-hydrazine; and
    (1-naphthyl)-hydrazine;
or an acid addition salt or hydrate thereof; in an amount effective to promote seed germination.

3. A method of claim 1 wherein said seeds are soybeans.

4. A method of claim 2 wherein said seeds are soybeans.

* * * * *

UNITED STATES PATENT AND TRADEMARK OFFICE
CERTIFICATE OF CORRECTION

PATENT NO. : 4,531,963

DATED : 30 July 1985

INVENTOR(S) : D.P. Wallach

It is certified that error appears in the above-identified patent and that said Letters Patent is hereby corrected as shown below:

Column 4, line 6, "(214-247)" should read -- (217-247) --.

Signed and Sealed this

First Day of July 1986

[SEAL]

Attest:

DONALD J. QUIGG

Attesting Officer

Commissioner of Patents and Trademarks